United States Patent [19]

Jordan

[11] Patent Number: 4,774,229

[45] Date of Patent: Sep. 27, 1988

[54] MODIFICATION OF PLANT EXTRACTS FROM ZYGOPHYLLACEAE AND PHARMACEUTICAL USE THEREFOR

[75] Inventor: Russell T. Jordan, Fort Collins, Colo.

[73] Assignee: Chemex Pharmaceuticals, Inc., Denver, Colo.

[21] Appl. No.: 860,654

[22] Filed: May 7, 1986

Related U.S. Application Data

[63] Continuation of Ser. No. 365,784, Apr. 5, 1982, abandoned, which is a continuation-in-part of Ser. No. 49,886, Jun. 19, 1979, abandoned.

[51] Int. Cl.$^4$ .................. A61K 31/70; A61K 31/33; A61K 31/28; A61K 31/30
[52] U.S. Cl. .................. 514/25; 514/183; 514/492; 514/499; 514/500; 514/503; 514/505; 514/660; 514/661; 514/734; 424/131; 424/140; 424/144; 424/145; 424/195.1; 536/8; 536/121
[58] Field of Search ............... 514/25, 183, 734, 492, 514/499, 500, 503, 505, 660, 661; 536/8, 121; 424/195.1, 140, 131, 144, 145

[56] References Cited

U.S. PATENT DOCUMENTS

| | | | |
|---|---|---|---|
| 3,808,197 | 4/1977 | Feaer et al. | 536/8 |
| 4,153,788 | 5/1979 | Courbat et al. | 536/8 |
| 4,229,437 | 10/1980 | Likens et al. | 424/145 |

OTHER PUBLICATIONS

Johnson, Cancer Treatment Reviews, 2:1–6, 1975.
Edwards, J. Nat. Prod., 42(1):85–91, 1979.
Sakakibara et al., Chem. Abst. 87:P180644r, 1977.
Saleh et al., Chem. Abst. 87:P180727v, 1977.
Bohnstedt et al., Chem. Abst. 92:P3193a, 1980.

*Primary Examiner*—John Rollins
*Attorney, Agent, or Firm*—Kenyon & Kenyon

[57] ABSTRACT

A mixture of an extract from a plant belonging to the Zygophyllaceae family containing phenolic compositions and a nonalkali metal salt is useful as a pharmaceutical agent, for example, in the treatment of cancer, nonmalignant tumors, osteomyelitis, psoriasis and warts.

21 Claims, No Drawings

MODIFICATION OF PLANT EXTRACTS FROM ZYGOPHYLLACEAE AND PHARMACEUTICAL USE THEREFOR

CROSS-REFERENCE TO RELATED APPLICATIONS

This is a continuation of application Ser. No. 365,784 filed Apr. 5, 1982, now abandoned, which is a continuation-in-part of application Ser. No. 049,886 filed on June 19, 1979, now abandoned.

FIELD OF THE INVENTION

This invention relates to a mixture of an extract from a plant belonging to the Zygophyllaceae family containing phenolic compositions and a metal salt. The mixture is useful as a pharmaceutical agent, for example, in the treatment of cancers, non-malignant tumors, osteomyelitis, psoriasis and warts.

BACKGROUND ART

Man has for centuries utilized plants as a source of medicaments for the treatment of essentially every affliction. Extracts and teas prepared from species of the plant genus Larrea (also known as chaparral and creosote bush) have been reported to have been used by Indians in the treatment of a variety of ailments including rheumatism, tuberculosis, cancer, sinus conditions, chronic backaches, kidney infections, prostate gland trouble, etc. Chaparral tea has also been reported in the last decade to be useful in the treatment of human cancer; however, subsequent studies conducted as a result of the alleged anticancer activity have concluded that the tea is not beneficial in the treatment of cancer. Extracts from Larrea plants, including nordihydroguaiaretic acid (NDGA), have also been investigated for potential antibacterial activity and have been found to possess such activity in vitro. Additionally, phenolic compositions having lignan and flavonoid structures, which are found in plants, have been investigated for their potential biological and pharmacological activity. A variety of activities have been reported including antiviral for some flavonoids, antimicrobial for some phenols and antitumor for some lignans and some phenols. However, much of this work has been conducted in vitro on a cellular level with different conclusions being drawn by different investigators. In fact, a recent article, *J. Nat. Prod.*, 42:85-91 (1979), which collated the results of 217 flavonoids tested in the screening program of the National Cancer Institute, concluded not only that no correlation could be drawn between KB cytotoxicity screens and animal screens for antitumor activity of flavonoids, but that flavonoids do not warrant further investigation as antitumor agents.

Zinc chloride and other escharotics have been utilized as treatments for cancer but, except as used in controlled applications in chemosurgical techniques, such uses generally have been condemned by the medical profession. Zinc chloride, including zinc chloride mixed with an extract from podophyllum, has been used as a fixative in chemosurgical removals of cancerous skin growths with layers of the growths being removed within a short period of time after each application of the fixative.

Additionally, the ability of a wide variety of metals have been investigated for their potential to chemically react with oxygen containing substituents of various compositions. However, none of the prior art teaches or suggests a mixture comprised of a Zygophyllaceae plant extract containing phenolic compositions and a metal salt. Nor does the prior art suggest the usefulness of such a mixture as a pharmaceutical agent useful in the treatment of cancer, tumors and osteomyelitis.

DISCLOSURE OF THE INVENTION

This invention relates to a mixture comprised of an extract from plants of the Zygophyllaceae family and a metal salt. More particularly, the present invention relates to a mixture of a metal salt wherein the metal is a multivalent metal and an extract from a plant of the Zygophyllaceae family which contains phenolic compositions having at least one hydroxy group attached to a benzene or adjacent to a carbonyl grouping conjugated to a benzene ring.

Zygophyllaceae is an established biological family and includes genera such as Fagonia, Guaciacum, Kallstroemia, Larrea, Peganum, Porlieria and Tribulus. Preferred plant extracts are those obtained from the leaves or stems of plants of the Larrea genus. Species within that genus include *L. nitida, L. ameghinoi, L. divaricata, L. tridentata* and *L. cuneifolia*.

Examples of phenolic compositions found in these plants and one or more of which are contained in the extracts of the mixtures of the present invention include, guaiacol, guaiaconic acid and lignans such as: nordihydroguaiaretic acid, guaiaretic acid, norisoguaiacin, 3'-demethoxyisoguaiacin, dihydroguaiaretic acid, partially demethylated dihydroguaiaretic acid, 1-(4(or 3)-hydroxyphenyl)-6,7 dihydroxy-2,3-dimethyl-1,2,3,4-tetrahydronaphthalene, 1-(3,4-dihydroxyphenyl)-6,7-dihydroxy-2,3-dimethyl 1,2,3,4tetrahydronaphthalene, 1-(3,4-dihydroxyphenyl)-2,3-dimethyl-4-(4(or 3)-hydroxyphenyl) butane, 1-(3,4-dihydroxyphenyl)-2,3-dimethyl-4-(3,4,5-trihydroxy-phenyl) butane, 1-(3,4-dihydroxyphenyl)-2,3-dimethyl-4-[3(or 4)-(4(or 3)-hydroxy-3(or 4)-methylbenzyloxy)-4(or 3)-hydroxyphenyl] butane and 1-(3(or 4)-acetoxy-4(or 3)-hydroxyphenyl)-2,3dimethyl 4-(3,4-dihydroxyphenyl) butane. The phenolic compositions found in the extracts also include flavonoid aglycones and flavonoid glycosides including, for example: quercetin, quercetagetin, gossypetin 3,7,3'-trimethyl ether, gossypetin 3,7-dimethyl ether, herbacetin 3,7-dimethyl ether, quercetin 3,7,3',4'-tetramethyl ether, quercetin 3,7,3'-trimethyl ether, quercetin 7,3',4'-trimethyl ether, quercetin 3,7-dimethyl ether, quercetin 3,3'-dimethyl ether, quercetin 7,3'-dimethyl ether, quercetin 3'-methyl ether, kaempferol 3,7-dimethyl ether, kaempferol 3,4'-dimethyl ether, kaempferol 3-methyl ether, kaempferol 7-methyl ether, kaempferol, luteolin 7,3'-dimethyl ether, luteolin 3'-methyl ether, apigenin 7-methyl ether, apigenin, dihydromyricetin 3,'5'-dimethyl ether, vicenin, chrysoeriol 6,8-di-C-glucoside, kaempferol 3-O-rhamnosylglucoside (nicotiflorin), isoquercitrin, rutin and isorhamnetin 3O-rhamnosylglucoside.

Preferred extracts are those which contain one or more of the following phenolic compositions: guaiacol, nordihydroguaiaretic acid, guaiaretic acid, norisoguaiacin, 3'-demethoxyisoguaiacin, dihydroguaiaretic acid, partially demethylated dihydroguaiaretic acid, 1,4-bis(-3(or 4)-hydroxy-4(or 3)-methoxyphenyl) butane, 1-(3,4-dihydroxphenyl-4-(3(or 4)-methoxy-4(or 3)-hydroxyphenyl) butane, 14(or 3)hydroxyphenyl)- 6,7-dihydroxy-2,3-dimethyl-1,2,3,4-tetrahydronaphthalene, 1-(4,4-dihydroxyphenyl)-6,7-dihydroxy-2,3-dimethyl- 1,2,3,4-tetrahydronapthalene, 1-(3,4-dihydroxyphenyl)-2,3-dimethyl-4-(4(or 3)-hydroxyphenyl) butane, 1-(3,4-dihydroxy-phenyl)-2,3-dimethyl-4(3,4,5-trihydroxyphenyl) butane, 1-(3,4-dihydroxyphenyl)-2,3-dimethyl-4-[3(or 4)-(or 3)-3(or 4)-methyl-benzyloxy)-4(or 3)-hydroxyphenyl] butane and quercetin.

The metal salts utilized in the mixtures of the present invention have as the metal component a multivalent nonalkali metal which is a halide. Examples of the metal portion of the salt include antimony, copper, cadmium, manganese and zinc. The preferred salt is chloride. The preferred metal salt is zinc chloride. When the mixture is to be applied topically as, for example, in the treatment of a tumor, wart or microbial affliction of the integument, it is preferred that the metal salt has the ability to exert an escharotic or keratolytic action on the skin.

Any type of extraction process which will extract phenolic composition(s) may be used and many such techniques are known. With the exception of the flavonoid glycosides, the phenolic compositions contained in the plants are generally not very soluble in water. Nevertheless, they can be obtained by an aqueous extraction process as for example, that disclosed in U.S. Pat. No. 2,382,475 which is incorporated herein by reference. With respect to some of the plants of the Zygophyllaceae family, for example, those of the Guaiacum genus, an extract containing phenolic compositions may be obtained by heating the desired plant part, e.g. the wood. The extracts from some plants, e.g. those of the Larrea genus, can be obtained by grinding the leaves and/or stems to obtain a powder. The powder is considered as an extract.

The desired phenolic compositions may also be obtained by an alcoholic extraction of the plant by slow percolation with alcohol as the menstruum until the ground plant is exhausted of its resin. The percolate is concentrated by evaporation until the residue has the consistency of a thin syrup. This thin syrup is then poured, with constant stirring, into an excess of water which is at a temperature of less than about 10° C. and which is slightly acidified with 37% reagent grade hydrochloric acid. The precipitate is then allowed to settle, the clear liquid is decanted and the precipitate is washed with cold water. The resin is then dried and powdered. It is the powder which is mixed with a metal salt to form the mixture of the present invention.

Double extractions of species of Larrea result in preferred extracts of the plant. These extracts are prepared by extracting the plant with a mixture of a lower alkyl substituted benzene and a lower alkyl semi-polar compound, removing the extract to recover the gum, and dissolving the gum in a lower alkyl alcohol, such as absolute ethanol, to produce a precipitate which contains phenolic compositions. The amount of extractant used per pound of creosote bush powder can vary widely, for example, from 0.25:1 to about 100:1 extractant to powder.

The original extractants include toluene, xylene, isopropyl benzene, cymene, ethyl benzene, and the like. The semi-polar solvents include ether, esters and the aprotic solvents such as dimethyl sulfoxide or dimethyl formamide. Among the useful ethers are the lower alkyl ethers such as methyl ether, methyl ethyl ether, ethyl ether, ethyl propyl ether and the like. Useful ketones include methyl ketone, ethyl ketone, methyl ethyl ketone and the like. Suitable esters include methyl acetate, ethyl formate, ethyl proponate and butyl acetate.

The lower molecular weight alcohols useful in removing less desirable portions of the creosote bush extract are methanol, ethanol and the propyl alcohols.

A preferred double extraction is with toluene and ether. This encompasses extracting the ground leaves and stems of the creosote bush with approximately 10 parts toluene and approximately 1 part anhydrous diethyl ether. The mixture of bush, toluene and diethyl ether is shaken for 24 hours and then the extract is filtered and the filtrate evaporated to dryness. Thereafter, the resulting residue is solubilized in absolute ethanol and the resulting cloudy suspension is heated until it is less turbid. This solution is then filtered and the filtrate cooled in a refrigerator at 5° C. or lower for at least 30 minutes. The cooling causes the precipitation of a white amorphous solid which is removed by filtration. The dark green clear solution which results is evaporated to dryness. The resulting residue contains phenolic compositions which can be mixed with a metal salt to form the mixture of the present invention. Additional extraction methods include those known by those skilled in the art, for example, those disclosed in U.S. Pat. Nos. 2,382,475; 2,421,109; and 2,421,117.

The residue from the extraction process can also be subjected to further processing to separate out specific phenolic compositions. These techniques are also known in the art, for example, those disclosed in U.S. Pat. Nos. 2,421,118; 2,444,346; and 2,644,822. An example of such a purification technique for dihydroguaiaretic acid can be found in *Anal. Chem.*, 23:2998 (1951) which is incorporated herein as a reference.

The mixtures are obtained by mixing the plant extract with a solution containing the metal salt to form a paste which may be further dried. Alternatively, mixtures of the present invention can be obtained by simply powdering that portion of the plant containing the phenolic compositions and then blending the powdered plant with a solution containing the metal salt. Generally a paste will be formed which can be further dried, for example by placing it in a humidified oven at 40° C. for a sufficient time to obtain the desired drying. The thus dried paste can be thereafter suspended in water by shaking it and then evaporated to near dryness on a rotary evaporator under reduced pressure.

The ratio of metal salt to extract is not particularly critical and will vary depending upon the composition of the extract, the metal salt and the expected use of the mixture. It is preferred that at least a portion of the metal salt, or themmetal salt in its ionized form, not be chemically reacted with the components of the extract. Generally, the metal salt will comprise from about 0.25 to about 75 weight percent of the mixture and preferably from about 20 to about 40 weight percent of the mixture.

In addition to the metal salt and the plant extract, the mixture can additionally contain chelatants and/or antioxidants. Examples of chelatants include urea, EDTA, various salts of EDTA, diethylenetriamine tetracetic acid (DTPA) and its various salts, nitrilotriacetic acid (NTA), ascorbate, salicyclic acid, citric acid, gluconic acid and amino acids. Examples of antioxidants include BHT (butylated hydroxytoluene), BHA (butylated hydroxyanisole), ascorbate, citric acid and ethoxyquin.

The novel mixtures of this invention are useful as antitumor agents and antimicrobials. They are useful against a wide variety of premalignant and malignant skin tumors, including senile keratotic lesions, basal cell carcinoma, squamous cell carcinoma and a diversified variety of melanotic lesions which are premalignant or malignant. The compounds are also effective against brain tumors, such as glioastrocytomas, anaplastic astrocytomas and glioblastomas, internal epithelial tumors of the gastrointestinal tract, pancreas, lungs, etc., breast cancer, cancer of the vulva, osteogenic sarcoma, bovine cancer eye, canine perianal adenomas and equine sarcoids. A variety of lymphadenopathies due to leukemias, lymphomas and infectious afflictions can be effectively treated with these mixtures.

As antimicrobials, the mixtures are useful in the treatment of osteomyelitis, psoriasis and warts.

The physiologically active mixtures of this invention should be present in amounts ranging from about 0.5 to 100 percent of a formulation. When applied topically, the drug will be contained in a pharmaceutically acceptable carrier, for example, a cream, ointment or solution. Polyethylene glycols or a mixture of polyethylene glycols are examples of suitable carriers for topical use. The frequency of application is dependent upon the condition being treated and the strength of the preparation. Generally, the compound will not be applied topically more often than once daily. The pharmacologically active substances used in this invention can be introduced, for oral medication, as a tablet, capsule, a syrup or as a food supplement. If the materials are to be injected, they can be injected in suitable solvent. These techniques are widely known and used. Capsules or tablets used for pharmaceutical formulations of the mixtures may be coated with one or more layers of materials, or incorporated into a matrix, using known techniques, to pass through one or more portions of the intestinal tract without dissolution and to dissolve in a particular portion of the tract. The capsules may contain microcapsules which release the pharmacologically active substances in one or more of the portions of the intestinal tract. The medicines to be given orally can have added thereto, additives, such as buffers, diluents, flavors, and color. Additionally, other materials may be added such as vitamins and antibiotics. The daily dosage of the pharmacologically active mixtures will vary depending upon the condition being treated, the severity of the condition, the particular pharmacologically active material used, and the route of administration. cl EXAMPLES In all of the following examples which relate to a plant extract, prior to the plant or plant material being subjected to an extraction process, it was first ground to a fine powder of from about 1–150 micron particle range, with the majority of the particles ranging from 1 to about 10 microns in size. The dried stems and leaves of *Larrea tridentata* or *divaricata* were ground with dry ice in a blender, then the particles of less than 10 millimeters in diameter were subjected to grinding with a ball mill until the desired fine powder was obtained.

EXAMPLE 1

Previously ground creosote bush (50 gm) was placed in a liter reagent bottle to which 500 milliliters of toluene and 50 milliliters of anhydrous diethyl ether were added. The bottle was stoppered and shaken for 24 hours on a reciprocating shaker. The toluene-ether extract was filtered through Whatman #1 filter paper. The filtrate was evporated to dryness on a rotary evaporator at 60° C. under reduced pressure. The resulting residue was solubilized in 100 milliliters of absolute ethanol. This cloudy suspension was heated gently causing the solution to become less turbid and then filtered through Whatman #1 filter paper. The filtrate was cooled in a refrigerator for 30 minutes. As a result of the cooling, a white amorphous solid was precipitated. This precipitate was removed by filtering with a Buchner funnel. The resulting clear dark green solution was evporated to dryness on a rotary evaporate at 60° C. under reduced pressure and then was finally dried in a 100° C. oven for 10 minutes. The resulting residue was weighed and then suspended in 100 milliliters of absolute ethanol. The catechol concentration was adjusted to 50 milligrams per milliliter with absolute ethanol. The adjustment of catechol content is not necessary. It was done as a means of standardizing the mixtures since the mixtures will vary due to the inherent variations of plant extracts.

The catechol content was determined by the method of Duisberg, P. C., et al. "Determination of Nordihydroguaiaretic Acid in the Leaf of *Larrea divaricata*", *Anal. Chem.*, 21:1393–96, which is incorporated herein as a reference.

EXAMPLE 2

A reagent consisting of 25 grams of potassium hydroxide and 12.5 grams of sodium pyrosulfite was added to 100 grams of previously ground *Larrea tridentata* in a 1,000 milliliter round-bottom flask. The flask was inserted into a heating mantle which had a voltage power supply of 40. A West condenser was attached to the top of the round-bottomed flask and cold water was circulated through the condenser. The material was allowed to reflux for 48 hours. While the extract was still hot, it was filtered through four layers of cheesecloth into a 1,000 milliliter beaker. When the cheesecloth became filled with extraction residue, the remaining extract was expressed by gentle squeezing or pressing. The extract appeared dark brown color and possessed the characteristic creosote bush odor. The contents of the beaker, which had a pH of about 10.3, were adjusted to a pH of 7.4 with concentrated hydrochloric acid.

EXAMPLE 3

Fifty grams of finely ground *Larrea tridentata* were percolated for 24 hours at a temperature of 37–40° C. with ethanol as the menstruum. The percolate was concentrated by evaporation until the residue had the consistency of a thin syrup. This syrup was poured, with constant stirring, into one liter of water which was at a temperatue of about 5° C. and which contained 10 ml of 37% reagent grade hydrochloric acid. The precipitate was allowed to settle. The clear liquid was decanted and the precipitate was washed with two one liter portions of cold distilled water. The resin containing phenolic compositions was then dried and powdered.

EXAMPLE 4

To 36.7 grams of powdered *Larrea divaricata* were added 24.5 grams of powdered rose hips and the mixture was blended in a blender for 5 minutes. The blended mixture was then mixed with 100 milliliters of an aqueous solution containing 185.9 grams zinc chloride to form a paste. The paste was allowed to stand at room temperature for 24 hours. Thereafter, it was stirred and then placed in a screw-capped glass container. The container was placed in a humidified oven at 40° C. for 5 days. This incubated paste was then suspended in 50 milliliters of triple distilled water and shaken at room temperature for 24 hours on a reciprocating shaker. The zinc chloride extract solution was then evaporated to near dryness on a rotary evaporator at 90° C. under reduced pressure. A sufficient quantity of this dried zinc chloride extract was added to 120 grams of an ointment base consisting of 10% (w/w) stearyl alcohol and 90% (w/w) polyethylene glycol to obtain an ointment containing 70% (w/w) of the extract.

EXAMPLE 5

The product of Example 1 was assayed for its catechol content and then was adjusted with ethyl alcohol to a solution containing 50 milligrams of catechol per milliliter of ethyl alcohol. To 75 milliliters of this solution was added 25 milliliters of an aqueous solution containing 2 grams of zinc chloride per milliliter. The final solution contained 5 milligrams of zinc chloride and 37.5 milligrams of catechol per milliliter of solution. When subjected to a high pressure liquid chromatographic analysis (HPLC), the solution exhibited a different elution pattern from the extract of Example 1. The HPLC analyses were conducted on a $C_{18}$ Microbondapak (brand name of the Waters Company), and the solvent, consisting of 53% acetonitrile and 47% water, had a flow rate of 1.5 milliliters per minute.

EXAMPLE 6

A sufficient quantity of the paste of Example 4 was added to sterile deionized water to obtain a concentration of 10 grams per 100 milliliters of water. The aqueous mixture was thoroughly shaken for one hour on a reciprocating shaker, then the aqueous suspension was filtered through Whatman #1 filter paper in a Buchner funnel. The filtrate, an aqueous suspension, was used to irrigate wounds in the treatment of osteomyelitis.

EXAMPLE 7

Five selected patients with osteomyelitis of duration of from several months to several years were treated topically with the solution of Example 6 and/or the paste of Example 4. In all instances, the osteomyelitis had been unresponsive to conventional treatment, and after the application of the mixture of the plant extract and zinc chloride, the patients received no other conventional therapy except as indicated. In some cases, the wounds were debrided, prior to the application of the metal and plant extract mixtures. Upon application of the metal and plant extract mixture, all of the patients experienced varying degrees of pain and a burning sensation over area which has been treated and some patients additionally experienced swelling and inflammation. One patient experienced severe nausea after the application.

Summaries, histories, and treatment are given below in Table 1. With respect to patient one, the disease process was so extensive that prior to treatment, a partial amputation of his foot was indicated. With respect to patient four, the disease process was so extensive as to cause the exposure of the extensor tendons which normally necessitates their cutting. Moreover, as a result of the destruction of the bones of the ankle and foot, the possibility of an ankle fusion was considered; however, neither of these procedures was required as the patient became ambulatory without the assistance of either a cane or crutches within six months of the beginning of the treatment with the mixture.

TABLE 1

| Patient | Diagnosis | Culture | Previous Treatment | Duration of Condition | Number of Treatments with the Metal-Extract | Time Required for Healing of Lesion |
|---|---|---|---|---|---|---|
| 1 (62 yr. male) | Chronic diabetic ulcer of left foot with osteomyelitis extending down to the metatarsal head capsule, involving the flexor tendon of the fourth toe | Hemolytic Staphylcoccus aureus coagulase positive | Antibiotics with no response | Several months | 2:13 days apart | 1½ months |
| 2 (59 yr. old male) | Chronic ulceration of lateral aspect of the proximal fibula | Staphylcoccus aureus coagulase positive | Multiple skin graftings; multiple antibiotics | Several years | 3:19 and 23 day apart | 3 months |
| 3 (63 yr. old male) | Chronic osteomyelitis of left ankle and distal tibia | Hemolytic Staphylcoccus aureus coagulase positive | Recent treatment with Betadine soaks | 35 years | 4:over a 3-month period (first two solution and last two with the paste) | 9½ months for complete recovery |
| 4 (70 yr. old female) | Ulcer of the left foot with necrosis, drainage, destruction of the bones of the foot and ankle initiated by a bite from a brown recluse spider | Hemolytic Staphylcoccus aureus coagulase positive | Antibiotics and soaks | 7 months | 2:5 days apart | 1½ months for lesions after 6 months able to walk without crutches<br><br>2½ months |
| 5 | Stasis ulcers of lower left extremity due to circulatory impairment | — | Steroid | Unknown | 2:9 days apart. Treated with a duiretic and soaks were applied | |

TABLE 1-continued

| Patient | Diagnosis | Culture | Previous Treatment | Duration of Condition | Number of Treatments with the Metal-Extract | Time Required for Healing of Lesion |
|---|---|---|---|---|---|---|
| | | | | | to the area to reduce swelling apparently caused by the treatment. | |

EXAMPLE 8

Fifteen older dogs having perianal adenomas were treated topically with the ointment of Example 4 having a strength of 55% (w/w) of the extract and zinc chloride and 45% (w/w) of the ointment base. The normal treatment for such a condition is surgery; however, these older dogs were poor surgical risks. The tumor of each dog was biopsied and the ointment was applied topically into the biopsied incision. The duration of treatment varied depending upon the severity of the adenoma. Dogs with simple circumscribed adenomas required only one treatment. The dogs with more advanced adenomas generally required more than one treatment which were given three to five days apart. The treatment was not successful in two of the dogs which had extremely advanced cases of perianal adenomas. The treatment was successful for the other thirteen dogs.

EXAMPLE 9

An incubated paste of rosehips, zinc chloride and *Larrea divaricata* prepared in accordance with the method of Example 4 was placed into gelatin capsules such that each capsule contained 200 mg. of the paste. A patient with glioastrocytoma was treated orally with these capsules. Prior to this treatment the patient had a resistant tumor which displaced the cranium and protruded from the right lateral aspect of the skull; the protrusion measured 7×7 mm. The patient received 200 mg. oral doses four times a day for a total daily dose of 800 mg. Objective and subjective improvement was seen within seven days; in 71 days the tumor had become cystic and lysed. The protuberance of the skull was reduced to near normal dimensions by repeated aspirations of the clear amber cystic tumor fluid. The patient was maintained on the 200 mg capsules given four times daily and remained symptom free for over 18 months.

EXAMPLE 10

Ten different human patients having skin cancer, eight of whom had basal cell carcinomas and two of whom had epidermoid carcinomas, had their tumors treated topically with an ointment comprised of about 54 grams of zinc chloride, 5 grams quercetin, 10 grams NDGA, about 10 grams ascorbic acid, about 20 grams of water and about 8 grams of polyethylene glycol.

With the exception of one patient, all of the patients received only one topical application of the ointment. One of the patients with the epidermoid carcinoma received 2 applications of the ointment, one month apart. All of the treatments resulted in the total disappearance of the tumors. The patients were observed for a minimum of about three months and some for as long as nine months. None of the patients experienced any recurrence of this tumor during that observation period.

EXAMPLE 11

A 64 year old male Caucasian with adenocarcinoma of the right lung was treated with a preparation comprised of zinc chloride, NDGA and ascorbic acid. The preparation was prepared by blending to obtain a homogeneous mixture 54 grams of zinc chloride, about 28 grams of water, about 11 grams of NDGA and about 7 grams of ascorbic acid. Capsules were prepared by placing 250 milligrams of the preparation in each capsule. The patient received a capsule five times daily for fourteen days. The treatment resulted in marked reduction in the tumor size as evidenced by X-rays; however, the patient died from complications.

EXAMPLE 12

Another group of human patients having skin cancers, twenty-one of whom had basal cell carcinomas and one of whom had an epidermoid carcinoma, were treated with a preparation comprising about 55 grams of zinc chloride, about 5 grams of quercetin, about 1 gram of NDGA, about 1 gram of ascorbic acid and 20 grams of water all formulated into about 15 grams of a base prepared from polyethylene glycol (PEG).

The basal cell carcinomas were treated topically twice. The length of time between applications varied from ten days to about four months. Twenty of the patients experienced total disappearance of their skin tumors. One patient did not complete the follow-up program and the results of his treatment are unknown. The other twenty patients who had successful treatments were observed for time periods ranging from about three to about twelve months after their last treatment and none experienced any recurrence of their tumors.

The patient with epidermoid carcinoma had an extremely large tumor which had practically destroyed all of his nose prior to the initiation of treatment. The carcinoma was treated topically three times with two months occurring between the first and second treatments and about ten weeks occurring between the second and third treatments. The patient did not respond to the treatment.

EXAMPLE 13

Another series of patients having a variety of skin afflications were treated topically with the preparation described in Example 12. Fifteen patients were treated for basal cell carcinomas. The preparation was applied from one to three times with applications being made from seven days to about a month and a half apart. With the exception of one patient, all of the treatments were successful resulting in the disappearance of the tumors and no evidence of recurrence five to ten months later.

The one patient for whom the treatment was not successful was a 79 year old male, who died of pneumonia ten days after treatment.

Three patients with epidermoid carcinoma of the skin were treated topically with the preparation. The treatment was successful in two of the patients resulting in disappearance of the tumors with no observable recurrence six to seven months after treatment. Another patient had numerous lesions requiring two applications of the preparation approximately two months apart. Although the tumors of this patient were treated successfully initially additional lesions did occur approximately thirteen months after treatment.

EXAMPLE 14

A preparation of an extract of *Larrea divaricata* and zinc chloride comprising 54.65 weight percent zinc chloride, 27.3 weight percent deionized water, 10.8 weight percent *Larrea divaricata* and 7.25 weight percent ascorbic acid was prepared as follows: Zinc chloride was totally dissolved in the deionized water; the ascorbic acid was added thereto to form a clear solution; and the *Larrea divaricata* was ball milled to a fine powder (approximately 20 micron diameter particles) and added to the solution to form the resultant paste.

EXAMPLE 15

The mixture of Example 14 (identified as Mixture 1 in Table 2), in addition to controls, was treated against xenografts of the transplantation established LX-1 human lung carinoma and MX-1 human mammary carcinoma in athymic nude mice of Balb/c background. Each animal was innoculated intradermally on the dorsum near the nape of the neck with 0.05 ml of a LX-1 tumor homogenate. The tumors were allowed to grow until they had established progressive growth defined in the first experiment as tumors having weights within a range of 100 to 567 (mg). Tumor weights, in milligrams, were calculated from the measurement of the length (L), width (W), and height (H), in millimeters, of the tumors using the formula (L×W×H)/2. The animals were randomized in groups to ensure representation of smaller and larger tumors within the weight range specified.

Topical treatment of the tumors was utilized and to assure penetration of the mixtures, the tumors were punctured with an 18-gauge (1½") needle to a depth slightly about the bevel (3/16"). The number of punctures varied form 8 to 12 depending on the size of the tumor. In the experiement (Table 2), the animals were treated twice, 18 and 19 days after LX-1 tumor innoculation. The results of the experiment are given below in Table 2. The mean delta tumor weight is the difference in tumor weight between the day specified and the mean tumor weight on the day of treatment. The tumor growth inhibition (positive or zero mean delta tumor weight) is expressed as % T/C value calculated from the average test delta TW/average control delta TW and may be positive or zero. Tumor regression (negative delta TW) is expressed directly as a percentage of the test change in the initial tumor weight and is preceeded by an R. The mixture is compared to the control of PEGA and crude Larrea plant.

TABLE 2

| Mixture | DAY OF FIRST TREATMENT | | | 15 DAYS AFTER 2ND TREATMENT | | | |
|---|---|---|---|---|---|---|---|
| | No. of Mice | Tumor Wt. (mg) Range | Mean delta Tumor Weight | No. of Mice | Mean Tumor Wt. (mg) | Mean delta Tumor Wt. (mg) | % T/C |
| 1 | 8 | 126–550 | 308 | 2 | 306 | −2 | R1% |
| Untreated Control | 16 | 144–486 | 284 | 15 | 1009 | −725 | — |
| PEGO Control | 8 | 172–446 | 300 | 7 | 1114 | +814 | — |
| PEGO + Control | 8 | 126–446 | 294 | 8 | 782 | +488 | — |

EXAMPLE 16

Mixtures of toluene-ether extracts of *Larrea tridentata* and zinc chloride were prepared by mixing the extract with a portion of ethanol and mixing, while heating, to obtain a uniform, fluid mixture. The zinc chloride was then added, either as crystals or dissolved in water, while continuing to heat and stir until all the zinc chloride was dissolved. The mixture was then heated in a stream bath until sufficient solvent was evaporated to obtain a sticky paste having a weight of about 130–140 (w/w %) of the weight of the dry extract and zinc chloride. The sticky paste was then formulated into a PEGO having the desired consistency appropriate for the particular route of administration. The compositions in approximate weight/weight percentages of the mixtures are given in Table 4.

TABLE 3

| Mixture | $ZnCl_2$ | Extract | Solvent (EtOH/$H_2O$) | PEG |
|---|---|---|---|---|
| A | 42.7 | 28.5 | 11 | 17.8 |
| B | 33.5 | 22.2 | 8.7 | 35.4 |
| C | 22.3 | 14.9 | 5.7 | 57 |
| D | 38.3 | 25.6 | 19.2 | 17 |

EXAMPLE 17

The extract mixtures of Example 16 were tested for their antitumor activity in vivo in mice against B-16 and Sarcoma-180 solid tumor.

The B-16 melanoma and the Sarcoma-180 solid tumor were grown intradermally/subcutaneously in $BDF_1$ (C57BL/6×DBA/2) mice and Institute of Cancer Research mice, respectively. Each mouse was injected intradermally with about 0.01 ml of a saline suspension containing about $1 \times 10^6$ cells of the particular cancer cells per ml into a preshaven area on the back of the neck of the mouse. The tumors were allowed to grow until they had an approximate size of about 25 to about 100 square millimeters, calculated by the length of the tumor multiplied by the width of the tumor. On the first day of treatment, animals with tumor sizes outside of the size range were culled out and the remaining animals were randomly divided into control and test groups. The tumors usually reached the appropriate size at day 6 post tumor innoculation. At this time the tumors were punctured uniformly and then treated with either a test mixture or a PEGO (polyethylene glycol base) control by topical application to the surface of the tumor. Generally, two topical applications were made 24 hours apart and the materials were applied to obtain from about a 1 to a 2 millimeter coating over the surface of the tumor. The animals were thereafter observed and their weights, as well as the size of their tumors, were periodically measured.

The results are given in Table 4 and include the number (n) of animals within a treatment group of an experiment, the average tumor size in milligrams of the animals treated with the mixtures and the average tumor size of the control animals, the ratio multiplied by 100 of the average size of the tumors of the treated animals to that of the control animals (T/C), the percentage of both treated and control animals clear of tumor and the percentage of animals still surviving after a given time period. A T/C value of 42 or less is indicative of activity. The T/C values, the percentage of animals clear of tumor and the percentage of animals surviving were all determined on the same day for the same experiment and varied form 21 to 33 days post tumor innoclulation.

TABLE 4

| Mixture | n | T/C | Tumor Size (Control) | % Clear (Control) | % Survival (Control) |
|---|---|---|---|---|---|
| | | | Sarcoma-180 | | |
| A | 10 | 15 | 174 ± 374 | 60 | 90 |
| | | | (1149 ± 1114) | (10) | (70) |
| A | 10 | 30 | 264 ± 225 | 10 | 60 |
| | | | (668 ± 713) | (0) | (100) |
| A | 10 | 25 | 242 ± 461 | 70 | 100 |
| | | | (966 ± 535) | (10) | (100) |
| A | 10 | 16 | 235 ± 242 | 40 | 100 |
| | | | (1450 ± 594) | (0) | (90) |
| B | 9 | 72 | 1015 ± 242 | 0 | 100 |
| | | | (1417 ± 685) | (0) | (100) |
| C | 9 | 89 | 1270 ± 439 | 0 | 100 |
| | | | (1417 ± 685) | (0) | (100) |
| D | 8 | 4 | 54 ± 108 | 50 | 75 |
| | | | (1417 ± 685) | (0) | (100) |
| D | 5 | 18 | 172 ± 332 | 50 | 80 |
| | | | (934 ± 656) | (10) | (100) |
| B | 10 | 153 | 1483 ± 781 | 0 | 100 |
| | | | (969 ± 655) | (0) | (100) |
| C | 10 | 76 | 737 ± 623 | 0 | 100 |
| | | | (969 ± 655) | (0) | (100) |
| D | 5 | 3 | 33 ± 71 | 80 | 100 |
| | | | (969 ± 655) | (0) | (100) |
| | | | B-16 Melanoma | | |
| A | 10 | 0 | 0 | 100 | 50 |
| | | | (683 ± 425) | (0) | (25) |
| A | 3 | 55 | 359 ± 421 | 0 | 67 |
| | | | (647 ± 421) | (0) | (67) |

EXAMPLE 18

A five year old Rottweiler female dog who had lost the complete use of her right front leg due to osteogenic sarcoma and who was a candidate for euthanasia was treated with an extract of *Larrea tridentata* and zinc chloride. The preparation was prepared by taking the product of Example 5 and adding glycerol thereto in an amount sufficient to result in a product containing 25 mg of catechol and 2.5 ml of zinc chloride. This was then mixed with equal volumes of a solution containing 0.35 grams of sodium ascorbate per milliliter of water and DMSO (44/56 v/v %). Thus, the preparation contained 12.5 mg of catechol, 1.25 mg of zinc chloride and 0.175 grams of sodium ascorbate per ml of solvent comprised of ethanol, glycerol, water and DMSO (25/25/22/28 v/v %).

1.66 ml of the preparation was administrered intravenously to the dog. The I.V. administration resulted in a violent reaction and conventional shock therapy was administered to the dog. About 2 weeks after the I.V. administration of the mixture, the dog began using its leg, she was clinically improving and X-rays indicated that the cancer was decreasing. By 7 weeks after treatment the dog had experienced a weight gain of 7 kg, had only a slight limp and was increasing its exercise. About 9 weeks after the initial administration, there was rapid enlargement of the nodular area vicinity of the right front leg and metastatic lesions were detected in the lungs via X-rays. At this time the preparation was applied directly to a portion of the tumor and oral alternate day therapy was initiated. After day 4 of the oral alternate day therapy, the drainage become very marked and a histopathology of the exudate indicated that it consisted of degenerated tumor cells and inflammatory cells. Eleven days after the application of the drug to the tumor, the dog begain using its leg again. A couple of days later lytic areas of the bone were noted and a pathological fracture occurred about 5 days later. However, the dog become cyanotic and expired 3 months after the date of initial treatment.

What is claimed is:

1. A method for treating the growth of mammalian tumors selected from the group consisting of basal cell and epidermoid carcinomas of the skin, comprising topically contacting said tumors with a pharmacologically active amount of a mixture comprising an extract from a plant belonging to the family Zygophyllaceae and a nonalkali metal halide selected from the group consisting of halides of copper, manganese, cadmium, antimony and zinc.

2. The method of claim 1 wherein the mixture comprises an extract form a plant which is a species of the Larrea genus, the extract contains at least one phenolic composition having at least one hydroxy substituent attached directly to a benzene ring or a hydroxy substitutent adjacent to a carbonyl grouping conjugated to a benzene ring.

3. The method of claim 2 wherein said metal halide is zinc chloride.

4. The method of claim 1 wherein the extract contains at least one phenolic composition selected from the group consisting of guaiacol; guaiaconic acid; nordihydroguaiaretic acid; guaiaretic acid; norisoguaiacin; 3'-demethoxyisoguaiacin; dihydroguaiaretic acid; partially demethylated dihydroguaiaretic acid; 1-(4-hydroxyphenyl)-6,7-dihydroxy-2,3-dimethyl-1,2,3,4,-tetrahydronaphthalene; 1-(3-hydroxyphenyl)-6,7-dihydroxy-2,3-dimethyl-1,2,3,4-tetrahydronaphthalene; 1-(3,4-dihydroxyphenol)6,7-dihydroxy-2,3-dimethyl-1,2,3,4-tetrahydronaphthalene; 1-(3,4-dihydroxyphenyl)-2,3-dimethyl-4-(3-hydroxyphenyl) butane; 1-(3,4-dihydroxyphenyl)-2,3-dimethyl-4-(4-hydroxyphenyl) butane; 1-(3,4-dihydroxyphenyl)-2,3-dimethyl-4-(3,4,5-trihydroxyphenyl) butane; 1-(3,4-dihydroxyphenyl)-2,3-dimethyl-4-[3-(4-hydroxy-3-methylbenzyloxy)-4-hydroxyphenyl] butane; 1-)3,4-dihydroxyphenyl)-2,3-dimethyl-4-[3-(3-hydroxy-4-methylbenzyloxy)-4-hydroxyphenyl] butane; 1-(3,4-dihydroxyphenyl)-2,3-dimethyl-4-[4-(4-hydroxy-3-methylbenzyloxy)-3-hydroxyphenyl] butane; 1-(3,4-dihydroxyphenyl)-2,3-dimethyl-4-[4-(3-hydroxy-4-methylbenzyloxy)-3-hydroxyphenyl] butane; 1-(3-acetoxy-4-hydroxyphenyl)-2,3-dimethyl-4-(3,4-dihydroxyphenyl) butane; 1-(4-acetoxy-3-hydroxyphenyl)-2,3-dimethyl-4-(3,4- dihydroxyphenyl) butane; quercetin; quercetagetin; gossypetin-3,7,3'-trimethyl esther; gossypetin-3,7-dimethyl ether; herbacetin-3,7-dimethyl ether; quercetin-3,7,3',4'-tetramethyl ether; quercetin-3,7,3'-trimethyl ether; quercetin-3,3',4'-trimethyl ether; quercetin-3,7-dimethyl ether; quercetin-3,3'-dimethyl ether; quercetin-7,3'-dimethyl ether; quercetin-3'-methyl ether; kaempferol-3,7-dimethyl ether; kaempferol-3,4'-dimethyl ether; kaempferol-3-methyl ether; kaempferol-7-methyl ether; kaempferol; luteolin-7,3'-dimethyl ether; luteolin-3'-methyl ether; apigenin-7-methyl ether; apigenin; dihydromyricetin-3,5'-dimethyl ether; vicenin; chrysoeriol-6,8-di-C-glucoside; kaempferol-30-rhamnosylglucoside; isoquercetin; and rutin- and isohamnetin-3-O-rhamnosylglucoside.

5. The method of claim 4 wherein said metal halide is selected from the group consisting of chloride of copper, manganese, cadmium, antimony and zinc.

6. The method of claim 5 wherein said metal halide is zinc chloride.

7. The method of claim 1 wherein the metal halide comprises from about 20 to about 40 weight percent of the mixture and the plant extract contains at least one phenolic composition selected from the gorup consisting of guaiacol; nordihydroguaiaretic acid; guaiaretic acid; norisoguaiacin; 3'-demethoxyisoguaiacin; dihydroguaiaretic acid; partially demethylated dihydroguaiaretic acid; 1,4-bis (3-hydroxy-4-methoxyphenyl) butane; 1,4-bis(4-hydroxy-3-methoxyphenyl) butane; 1-(3-4-dihydroxyphenyl)-4-(3-methoxy-4-hydroxyphenyl) butane; 1-(3,4-dihydroxyphenyl)-4-(4-methoxy-3-hydroxyphenyl) 4-tetrahydronaphthalen; 1-(3-hydroxyphenyl)-6,7-dihydroxy-2, 3-dimethyl-1,2,3,4-tetrahydronaphthalene; 1-(4,4-dihydroxyphenyl)- 6,7-dihydroxy-2,3-dimethy-1,2,3,4-tetrahydronaphthalene; 1-(3,4-dihydroxyphenyl)-2,3-dimethyl-4-(4-hydroxyphenyl) butane; 1-(3,4-dihydroxyphenyl)-2,3-dimethyl-4-(3-hydroxyphenyl) butane; 1-(3,4-dihydroxyphenyl)-2,3-dimethyl-4-(3,4,5-trithydroxyphenyl) butane; 1-(3,4-dihydroxyphenyl)-2,3-dimethyl-4-[3-(3-methylbenzyloxy)-4-hydroxyphenyl] butane; 1-(3,4-dihydroxyphenyl)-2,3-dimethyl-4-[4-(3methylbenzyloxy)-4-hydroxyphenyl] butane; 1-(3,4-dihydroxyphenyl)-2,3-dimethyl-4-[3-(4-methylbenzyloxy)-3-hydroxyphenyl] butane; 1-(3,4-dihydroxyphenyl)-2,3-dimethyl-4-[4-(4methylbenzyloxy)-3-hydroxyphenyl] butane; and quercetin.

8. The method of claim 7 wherein said metal halide is selected from the group consistin of chloride of copper, manganese, cadmium, antimony and zinc.

9. The method of claim 8 wherein said metal halide is zinc chloride.

10. The method of claim 1 wherein said metal halide is a zinc halide.

11. A method for treating solid mammalian tumors of the skin which comprises topically administering to a mammal in need of said treatment a composition containing a pharmacologically active amount of nordihydroguaiaretic acid and a nonalkali metal halide selected from the group consisting of copper, manganese, cadmium, antimony and zinc.

12. The method according to claim 11 wherein said metal halide is zinc chloride.

13. The method according to claim 11 wherein the mammalian tumors are selected from the group consisting of adenomas, sarcomas, melanomas, basal cell carcinoma and epidermoid carcinoma.

14. A method for treating the growth of mammalian tumors of the skin comprising topically administering to a mammal in need of said treatment a composition containing a pharmacologically active amount of nordihydroguaiaretic acid and a zinc metal salt.

15. The method according to claim 14 wherein the zinc metal salt is zinc chloride.

16. A method for treating the growth of mammalian tumors of the skin selected from the group consisting of adenomas, sarcomas, melanomas, keratotic lesions, basal cell carcinoma and epidermoid carcinoma comprising the topical administration to a mammal in need of said treatment a composition containing a pharmacologically active amount of nordihydroguaiaretic acid and a zinc metal salt.

17. The method according to claim 16 wherein the zinc metal salt is zinc chloride.

18. A composition comprising nordihydroguaiaretic acid and a nonalkali metal halide selected from the group consisting of copper, manganese, cadmium, antimony and zinc.

19. The composition according to claim 18 wherein the nonalkali metal halide is zinc chloride.

20. A pharmaceutical composition comprising a pharmaceutically acceptable carrier and the composition of claim 18.

21. A pharmaceutical composition comprising a pharmaceutically acceptable carrier and the composition of claim 19.

* * * * *

UNITED STATES PATENT AND TRADEMARK OFFICE
CERTIFICATE OF CORRECTION

PATENT NO. : 4,774,229

DATED : Sept. 27, 1988

INVENTOR(S) : Russell T. Jordan

It is certified that error appears in the above-identified patent and that said Letters Patent is hereby corrected as shown below:

Column 2, line 18, delete "Guaciacum" and substitute therefor --Guaiacum--.

Column 2, line 34, delete "4tetrahydronaphthalene" and substitute therefor -- 4-tetrahydronaphthalene --

Column 2, line 66, delete "14 (or 3)" and substitute therefor -- 1-4(or 3) --.

Column 3, line 38, delete "residum" and substitute therefor --residue--.

Column 4, line 49, delete "themmetal" and substitute therefor --the metal--.

Column 5, line 44, delete "cl".

Column 6, line 6, delete "evporated" and substitute therefor --evaporated--.

Column 6, line 6, delete "evaporate" and substitute therefor --evaporator--.

UNITED STATES PATENT AND TRADEMARK OFFICE
CERTIFICATE OF CORRECTION

PATENT NO. : 4,774,229

DATED : Sept. 27, 1988

INVENTOR(S) : Russell T. Jordan

It is certified that error appears in the above-identified patent and that said Letters Patent is hereby corrected as shown below:

Column 6, line 36, between "brown" and "color", insert --in--.

Columns 11-12, Table 2, delete "PEGO + Control" and substitute therefor --PEGO + Crude Plant Control--.

Column 12, line 7, delete "PEGA" and substitute therefor --PEGO--.

Column 12, line 30, delete "stream" and substitute therefor --steam--.

Column 14, line 53, delete "(3,4-dihydroxyphenol) 6,7" and substitute therefor --(3,4-dihydroxyphenol)-6,7--.

Column 15, line 5, delete quercetin-3,3',4'" and substitute therefor --quercetin-7,3',4'--.

Column 15, line 15, delete "30-rhamnosylglucoside" and substitute therefore --3-O-rhamnosylglucoside--.

UNITED STATES PATENT AND TRADEMARK OFFICE
CERTIFICATE OF CORRECTION

PATENT NO.  : 4,774,229

DATED       : Sept. 27, 1988

INVENTOR(S) : Russell T. Jordan

It is certified that error appears in the above-identified patent and that said Letters Patent is hereby corrected as shown below:

Column 15, line 16, delete "isohamnetin" and substitute therefor --isorhamnetin--.

Column 15, line 34, after "methoxy-3-hydroxyphenyl)" and before "4-tetrahydronaphthalen", insert --butane; 1-(4-hydroxyphenyl)-6,7-dihydroxy-2,3-dimethyl-1,2,3,--.

Column 15, line 34, delete "4-tetrahydronaphthalen" and substitute therefor --4-tetrahydronaphthalene --.

Column 15, lines 45-46, delete "(3methyl-benzyloxy" and substitute therefor --(3-methylbenzyloxy --.

Column 15, line 49, delete "(4methylbenzyloxy)" and substitute therefor --(4-methylbenzyloxy)--.

Column 16, line 2, delete "consistin" and substitute therefor --consisting--.

Signed and Sealed this

Nineteenth Day of December, 1989

Attest:

JEFFREY M. SAMUELS

*Attesting Officer*    *Acting Commissioner of Patents and Trademarks*